US008602644B2
::::

(12) United States Patent  (10) Patent No.: US 8,602,644 B2
Choi  (45) Date of Patent: Dec. 10, 2013

(54) MULTIFUNCTIONAL MICROPIPETTE BIOLOGICAL SENSOR

(75) Inventor: Tae-Youl Choi, Frisco, TX (US)

(73) Assignee: University of North Texas, Denton, TX (US)

( * ) Notice: Subject to any disclaimer, the term of this patent is extended or adjusted under 35 U.S.C. 154(b) by 760 days.

(21) Appl. No.: 12/776,079

(22) Filed: May 7, 2010

(65) Prior Publication Data

US 2010/0285210 A1  Nov. 11, 2010

Related U.S. Application Data

(60) Provisional application No. 61/176,711, filed on May 8, 2009.

(51) Int. Cl.
- *G01K 7/02*    (2006.01)
- *G01K 13/00*   (2006.01)
- *G01N 27/26*   (2006.01)
- *G01N 33/483*  (2006.01)
- *G01R 1/06*    (2006.01)

(52) U.S. Cl.
USPC ...... 374/141; 374/142; 374/179; 374/E1.001; 374/E7.004; 73/863.32

(58) Field of Classification Search
USPC .......... 374/141, 142, 143, 179, E7.004, 374/E1.001; 73/863.32, 864.01; 422/501, 422/507, 922
See application file for complete search history.

(56) References Cited

U.S. PATENT DOCUMENTS

| | | | | |
|---|---|---|---|---|
| 3,666,651 A * | 5/1972 | Makabe | ......... | 204/420 |
| 4,613,238 A * | 9/1986 | Sachs | ......... | 374/174 |
| 4,816,131 A * | 3/1989 | Bomsztyk | ......... | 204/403.1 |
| 4,885,945 A * | 12/1989 | Chiodo | ......... | 73/863.32 |
| 5,119,819 A | 6/1992 | Thomas et al. | | |
| 5,986,261 A * | 11/1999 | Lewis et al. | ......... | 250/306 |
| 6,737,331 B1 * | 5/2004 | Lewis et al. | ......... | 438/404 |
| 7,421,905 B2 * | 9/2008 | Zerwekh et al. | ......... | 73/800 |
| 2002/0021222 A1 | 2/2002 | Howitz et al. | | |
| 2007/0006663 A1 * | 1/2007 | Zerwekh et al. | ......... | 73/800 |
| 2007/0059215 A1 | 3/2007 | Huang | | |
| 2010/0167412 A1 * | 7/2010 | Xiao et al. | ......... | 436/171 |
| 2010/0199788 A1 * | 8/2010 | Ayliffe et al. | ......... | 73/864.11 |
| 2012/0091008 A1 * | 4/2012 | Muir et al. | ......... | 205/316 |
| 2012/0225435 A1 * | 9/2012 | Seger et al. | ......... | 435/7.1 |

FOREIGN PATENT DOCUMENTS

WO       9505000 A1    2/1995
WO   WO 2005121780 A2 * 12/2005 ........... G01N 33/00

OTHER PUBLICATIONS

Fish, G., et al., "Ultrafast Response Micropipette-Based Submicrometer Thermocouple," Rev. Sci. Instrum. 99 (5), May 1995, pp. 3300-3306.

Watanabe, M.S., et al., "Micro-Thermocouple Probe for Measurement of Cellular Thermal Responses," Proceedings on the 2005 IEEE, Sep. 1-4, 2005, pp. 4858-4861.

* cited by examiner

*Primary Examiner* — R. A. Smith

(74) *Attorney, Agent, or Firm* — Edwin S. Flores; Chainey P. Singleton; Chalker Flores, LLP (57) ABSTRACT

The fabrication and use of a multifunctional micropipette biological sensor for in-situ detection of temperature changes, ion conductivity, and light is described herein.

10 Claims, 8 Drawing Sheets

EMPTY PIPETTE

FIG. 2A

FILLED PIPETTE

MULTIFUNCTIONAL MICROPIPETTE BIOLOGICAL SENSOR

CROSS-REFERENCE TO RELATED APPLICATIONS

This application claims priority to U.S. Provisional Application Ser. No. 61/176,711 filed May 8, 2009, the entire contents of which are incorporated herein by reference.

TECHNICAL FIELD OF THE INVENTION

The present invention relates in general to the field of physical and biological sensing, and more particularly to the design and fabrication of a novel glass micropipette sensor for in-situ detection of temperature changes, ion conductivity, pH and light.

STATEMENT OF FEDERALLY FUNDED RESEARCH

None

INCORPORATION-BY-REFERENCE OF MATERIALS FILED ON COMPACT DISC

None.

BACKGROUND OF THE INVENTION

Without limiting the scope of the invention, its background is described in connection with the design and use of a glass micropipette biological sensor for in-situ detection of temperature changes, ion conductivity, pH and light.

United States Patent Application No. 20070059215 (Huang, 2005) teaches a micro pipette sensing device that includes a micro pipette and a sensing device. The micro pipette includes a main portion, an operation portion and at least one tube portion. The tube portion defines an operation space comprising a sensing device that includes a MEMS flow sensor for sensing a gas movement in the operation space.

WIPO Publication No. WO9505000 (Aaron and Klony, 1999) discloses a general purpose force sensor for measuring nanometer scale surface topography and other characteristics. The sensor includes a hollow micropipette having an inner diameter of about 7.5 nanometers at its tip. The probe includes a cantilevered structure obtained by heating it near the tip to bend it. A reflective coating is applied to the outer surface of the micropipette.

United States Patent Application No. 20020021222 (Howitz and Burger, 2002) describes an apparatus for sensing a drop of liquid delivered by a micropipette, that comprises a sensor comprising of electrodes arranged in a selected geometric pattern on a surface of a substrate, wherein the electrodes are insulated from each other at the surface and an electronic analysis unit is coupled to the electrodes for sensing changed electrical characteristics between the electrodes which result from the drop of a liquid deposited on the surface.

U.S. Pat. No. 5,119,819 issued to Thomas et al. (1992) describes a micro-thermocouple for non-invasive monitoring of changes in blood glucose concentration in a tissue specimen and particularly in an individual. The method uses acoustic velocity measurements for monitoring the effect of glucose concentration upon the density and adiabatic compressibility of the serum.

SUMMARY OF THE INVENTION

The present invention provides an apparatus and method for making and using a thermal sensor having a multibarrel capillary tube; one or more glass micropipettes wherein the one or more micropipettes are enclosed within the multibarrel capillary tube, a metal junction at the tip of the one or more micropipettes and a metal coating on the outer surface of the one or more micropipettes of the thermal sensor.

The present invention includes a method of fabricating a micropipette thermal sensor by enclosing a glass micropipette within a multibarrel capillary tube; pushing a solid metal through a top open end of the glass micropipette; heating a lower tip end of the glass micropipette; melting the solid metal near the lower tip end; attaching the micropipette at an incline on the surface of a rotating disc comprising an ultrafine-grind sandpaper or other suitable grinding surface; grinding the extruded solid metal near the lower tip end; sharpening the micropipette; and coating an outer surface of the micropipette thermal sensor with a noble metal to manufacture a micropipette thermal sensor.

The present invention also includes a method of measuring temperature and temperature changes in a biological system in an aqueous medium by injecting a micropipette thermal sensor into a biological system in the aqueous medium; maintaining a constant temperature of the aqueous medium to ensure that the temperature or temperature changes are solely due to a biological activity in the biological system; monitoring the temperature of a cold junction; wherein the cold junction comprises the area between one or more lead wires, and one or more deposited and filled metals; compensating for a change in one or more signals due to the cold junction temperature change and measuring and compensating for a fluctuation in temperature to accurately measure the temperature or the temperature changes.

The present invention is also a micropipette sensor for measuring ion conductivity measuring having a multibarrel capillary tube; one or more glass micropipettes; wherein the one or more micropipettes are enclosed within the multibarrel capillary tube; a polymeric coating at the tip of the one or more micropipettes; and a metal coating on the outer surface of the micropipette sensor.

The present invention provides a method of fabricating a micropipette sensor for measuring ion conductivity by enclosing a glass micropipette within a multibarrel capillary tube; dipping a lower tip end of the glass micropipette in a polymer solution; washing the polymer at the lower tip end with an organic solvent; and coating an outer surface of the micropipette sensor with a noble metal.

The present invention provides a method of measuring ion conductivity in a biological system by injecting a micropipette sensor for measuring ion conductivity into a biological system; measuring an electrical impedance within the biological system; measuring the drop in the electrical impedance within the biological system; and correlating a change in the electrical impedance with the changes in an ionic composition and state of a biological system.

The present invention provides a micropipette optical sensor having an empty micropipette coated with a metal in a multibarrel micropipette. The present invention also provides a method of fabricating a micropipette optical sensor comprising the step of coating noble metal (Au or Ag) outside the multibarrel pipette to guide the light wave. The present invention provides a multifunctional micropipette sensor having a multibarrel capillary tube; three or more glass micropipettes; wherein the three or more micropipettes are enclosed within the multibarrel capillary tube; a metal junction at the tip of at least one of the three or more micropipettes; a polymer coating at the tip of at least one of the three or more micropipettes; and a metal coating on the outer surface of the multifunctional micropipette.

The present invention provides a method of measuring temperature and ion conductivity in a biological system by placing at least a part or the whole biological system in a chamber; placing one or more gold microelectrodes in the chamber; inserting a sample comprising deionized water into the chamber; injecting one or more multifunctional micropipette sensors into the biological system; measuring an electrical impedance within the biological system; measuring the drop in the electrical impedance within the biological system; correlating a change in the electrical impedance with the changes in an ionic composition and state of a biological system; and measuring a metabolic temperatures from a part or the whole biological system.

The present invention also provides a multifunctional micropipette sensor-scanning probe microscopy combination device having a scanning probe microscope and a multifunctional micropipette sensor. The method of the present invention can also be used to detect "hot" spots in a semiconductor sample using a multifunctional micropipette sensor by approaching a pipette tip of a multifunctional micropipette sensor to the semiconductor sample; maintaining a gap of at least tens of nanometers between the pipette tip and the semiconductor sample; regulating the distance with a scanning probe microscope; monitoring the generation of one or more thermocouple voltages in one or more hot spots in the semiconductor samples; scanning the semiconductor sample surface while maintaining the gap of at least tens of a nanometer between the pipette tip and the semiconductor sample; and detecting a temperature of one or more hot spots in the semiconductor sample.

The present invention provides a micropipette pH sensor having a multibarrel capillary tube; one or more glass micropipettes; wherein the one or more micropipettes are enclosed within the multibarrel capillary tube; one or more ion selective membranes at the tip of the one or more micropipettes; a metal coating on the outer surface of the micropipette pH sensor; and an electrolyte coated by electrolytic deposition on the outside of the metal coated micropipette pH sensor.

The present invention provides a method of fabricating a micropipette pH sensor by filling a small amount of one or more molten ion selective membranes into a pulled micropipette; heating the tip of the pulled micropipette; pressurizing the tip of the micropipette to force out the molten one or more ion selective membranes; curing a liquid droplet of the ion selective membrane at room temperature to form a solid membrane; coating an outer surface of the micropipette with silver; adding a coat of silver chloride by electrolytic deposition onto the silver coated outer surface; and beveling the outer surface to remove any excess extruded ion selective membranes or silver at the tip of the micropipette.

The present invention provides a method of fabricating an integrated temperature and ion-conducting sensor by providing a double barrel pipette; providing a micropipette thermal sensor; providing a micropipette ion-conducting sensor; inserting the micropipette thermal sensor in one of the barrels of the double barrel pipette; inserting the micropipette ion-conducting sensor in one of the barrels of the double barrel pipette; and beveling one end of the double barrel pipette to remove an extruded metal from the interior of the micropipette thermal sensor.

The present invention provides a method of fabricating an integrated temperature and pH sensor by providing a double barrel pipette; providing a micropipette thermal sensor; providing a micropipette pH sensor; inserting the micropipette thermal sensor in one of the barrels of the double barrel pipette; inserting the micropipette pH sensor in one of the barrels of the double barrel pipette; beveling both ends of the double barrel pipette; coating the beveled area of the pH sensor with a photoresist (e.g., AZ4562 or photoresists of similar thickness); depositing a metal on the outer surface of the double barrel pipette; depositing an electrolyte by electrolytic deposition on the outer surface of the double barrel pipette; and establishing a contact between one or more lead wires and the deposited metal layers.

The present invention provides a method of fabricating an integrated temperature, ion conducting and pH sensor by providing a multi barrel pipette; providing a micropipette thermal sensor; providing a micropipette pH sensor; providing a micropipette ion conducting sensor; inserting the micropipette thermal sensor in one of the barrels of the multi barrel pipette; inserting the micropipette pH sensor in one of the barrels of the multi barrel pipette; inserting the micropipette ion conducting sensor in one of the barrels of the multi barrel pipette; beveling the two ends of the multi barrel pipette; wherein the two ends comprise the micropipette thermal and pH sensors; coating the beveled area of the pH sensor with a photoresist; depositing a metal on the outer surface of the multi barrel pipette; depositing an electrolyte by electrolytic deposition on the outer surface of the multi barrel pipette; and establishing a contact between one or more lead wires and the deposited metal layers.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "micropipette" as used herein in its broadest sense refers to various kinds of pipettes capable of pipetting 100 μl or less of the sample and includes microelectrodes and microneedles with tips of ten microns or less outer diameter.

Figure 1A:
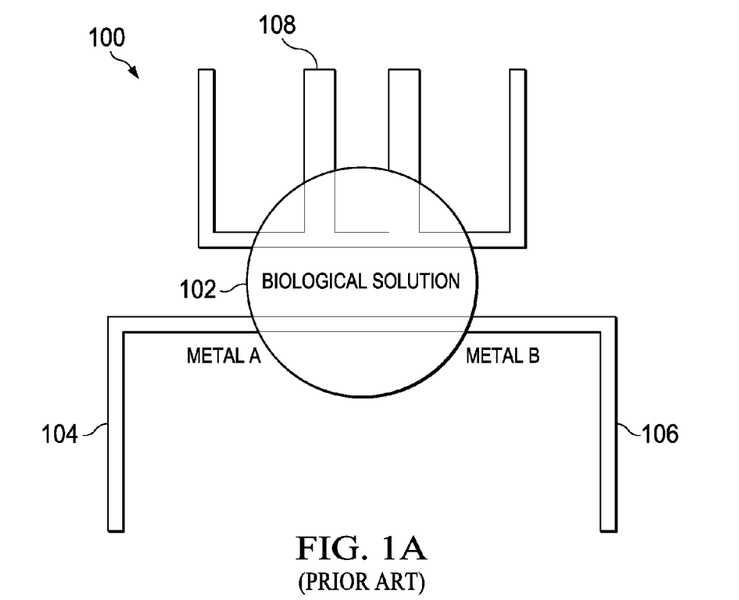
FIG. 1A represents a traditional prior art ion conducting biosensor composed of two meta microelectrodes.

Pulled micropipettes have been widely used in many biological applications for injecting biological solution into tissues. The biological sensors of the present invention comprise of glass micropipettes. FIG. 1A is a traditional ion conducting biosensor 100. A biological solution 102 is placed in contact with a first metal 104 (metal A) and in contact with a second metal 106 (metal B). The biological solution 102 is also in contact with sensor unit 108.

Figure 1B:
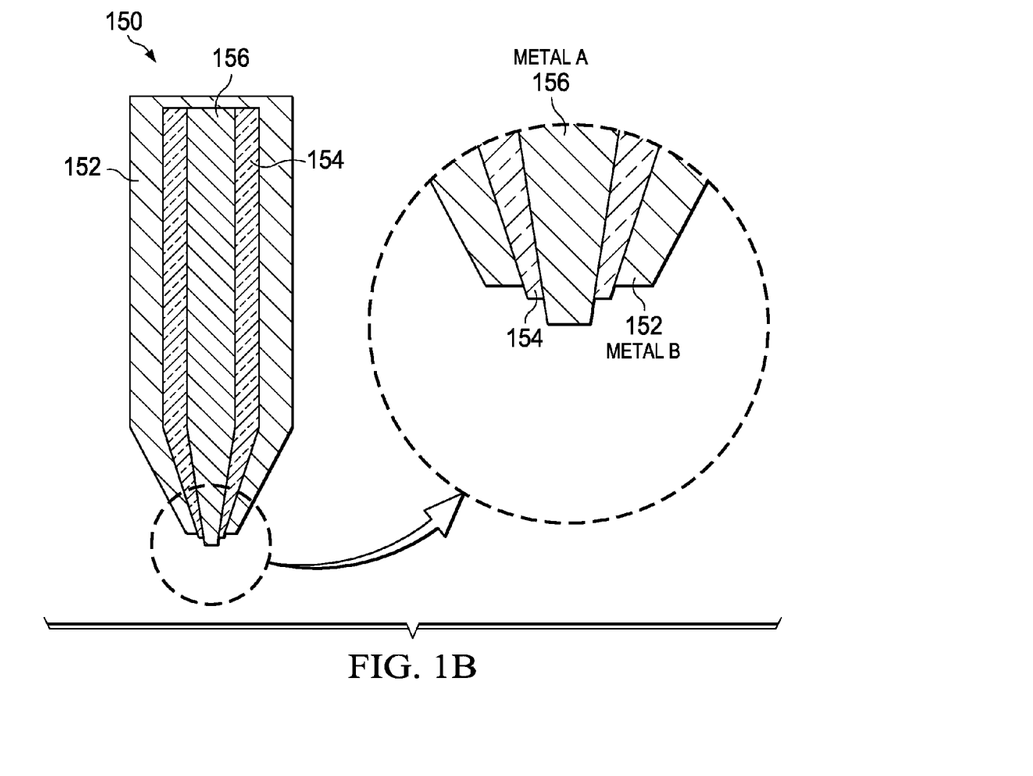
FIG. 1B is an expanded view of the sensing (ion conduction) tip of the micropipette biosensor of the present invention.

The present inventors have fabricated a micropipette thermal sensor (FIG. 1B). The micropipette thermal sensor 150 of the present invention comprises a glass micropipette 154 in which a hollow interior of the glass micropipette 154 is filled with a first metal 156 (metal A) and in which the outer surface of the glass micropipette 154 is covered with a second metal 152 (metal B).

Figure 2A:
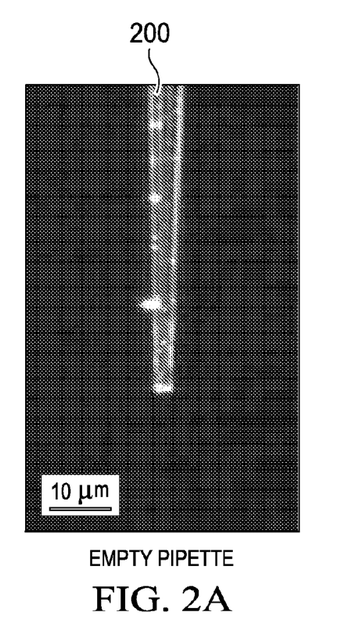
FIG. 2A shows a pulled glass micropipette for thermocouple temperature sensor of the present invention (an empty pipette with a ~3 μm opening)

FIG. 2A shows a micropipette 200 pulled by a micropipette puller (P-97, Sutter instrument). To function as a thermal sensor, a metal junction at the tip needs to be formed. A typical low melting-temperature soldering alloy of tin and lead (Sn:Pb) 256 was filled inside the pipette 254 by injection molding in conjunction with localized heating of the metal. The injection molding was realized by two ways: pressurized nitrogen gas and mechanical pushing. The former process requires that the molten metal is filled entirely the interior space of the pipette.

Figure 2B:
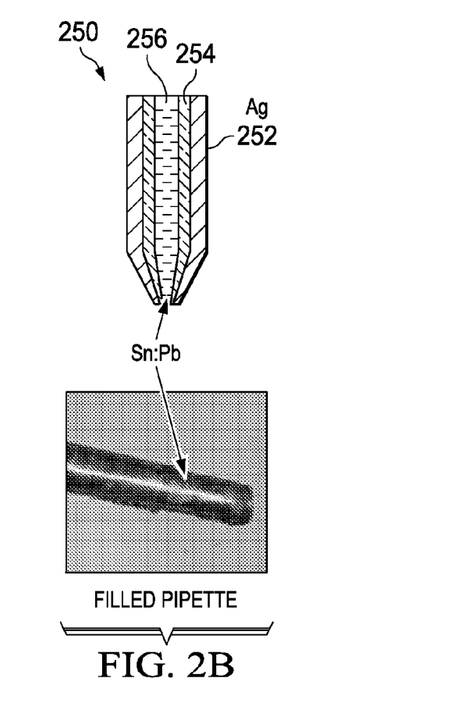
FIG. 2B shows a micropipette thermocouple temperature sensor of the present invention (filled pipette with solder alloy (inside) coated with Ag outside the pipette). The contact made at the tip functions as a temperature sensor.
Figure 2C:
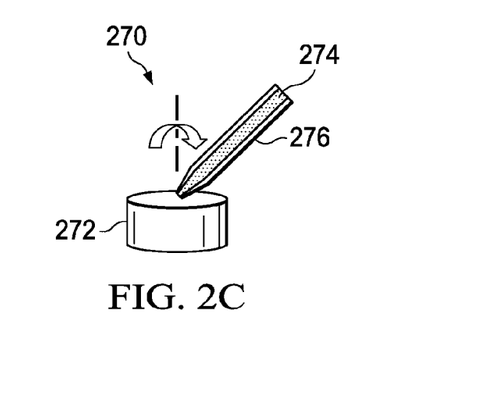
FIG. 2C is a schematic for beveling the tip of the temperature sensor shown in FIG. 2B.

In this case, the pressure needed to inject the molten metal out of the tip must be large enough to overcome the capillary force at the tip of the pipette. A much simpler manufacturing process was realized by pressurizing (or pushing) mechanically the solid metal at the top 250 of the pipette (FIG. 2B) while heating locally with a laser or an electronic soldering gun the lower part near the tip. Thus, only the metal near the tip is melt, in which a much less pressure is needed. The next step is to bevel the tip. The pipette 274 is attached into a 3-axis translational stage 270 and inclined by 45 degrees with respect to a rotating disk 272 to which an ultrafine-grid sand paper is attached (FIG. 2C). This step is necessary to grind unwanted metal extruded outside the pipette and sharpen the pipette so that it can be injected into the cell easily. Then, the outer surface 276 of the pipette 274 was coated with Silver (Ag) 252 in a sputtering chamber.

Current combination of metals (Ag and Sn:Pb) generated ~1 μV/K. To enhance the sensitivity and resolution of the sensor, a new combination of metals that exhibit a high Seebeck coefficient difference as well as biocompatibility was required. Bismuth is known as a biologically harmless substance and has a high Seebeck coefficient. Coating bismuth on the outer surface of the glass pipette can generate a large electromotive force, rendering a highly sensitive thermal sensor. Gold is generally not considered a good candidate because of its Seebeck coefficient although they are highly biocompatible, however, in certain applications they may have to be used. To prevent toxicity at the cellular level completely, the outside tip will be coated with a thin polymer layer. The sensor measures ion conductivity inside the biological tissue when no metal contact is made at the tip while both electrodes function as conductivity probes. These sensors are snug-fitted into the multifunctional head and mounted on a linear translational stage for injection contact with biological tissues. A snug-fit is realized by dipping only the very end of the tip into a polymer solution (such as photoresist) before coating a metal (Ag) on the outer surface of the pipette. After coating, the polymer is washed away by using acetone.

The manufactured sensors are calibrated in the next step. Because the lead wires (Copper) that are connected to a measurement instrument (voltmeter) are different from the coated and filled metals, the additional contacts (reference junction) are made between Copper and metals that also generate electromotive forces, which are compensated through hardware or software compensation devices, depending on the implantation. A small disk block made of aluminum is attached to the reference junction. A temperature sensor can also be attached to the block and the measured junction temperature will be used for compensation.

Figure 5A:
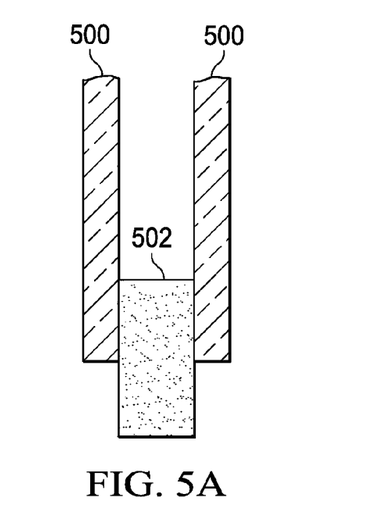
FIGS. 5A-5E shows a schematic of the fabrication steps of a pH sensor: (5A) ion selective membrane extrusion; (5B) Ag coating; (5C) beveling of the tip; (5D) enlarged view of tip section for pH sensor; (5E) an alternative design of pH sensor using double barrel pipette.
Figure 5B:
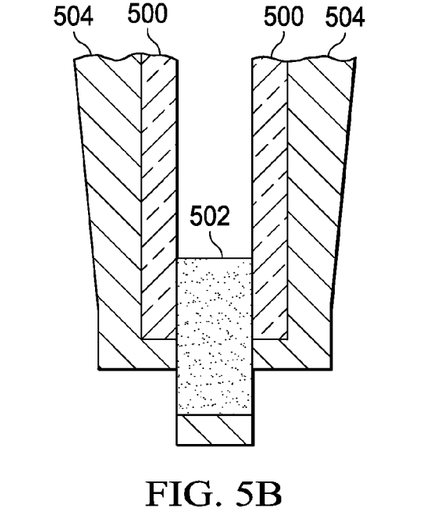

Development of pH sensors: A millisecond time response in intracellular pH measurement was demonstrated by using submicron fiber optic sensors [Tan et al., 1992]. This study employed an optical imaging technique where expensive scanning equipment and laser are required. On the contrary the sensor of the present invention utilizes an electrical sensing scheme, rendering an inexpensive sensing device. A schematic diagram of micropipette pH sensor with a size of ~1 μm is depicted in FIGS. 5A-5E. Initially a pulled micropipette 500 was filled with a small amount of ion selective membrane 502 (i.e., polyvinyl chloride (PVC) powder, or sodium calcium silicate liquid glass). As is similar to thermal sensor fabrication, the tip of the pipette was heated while pressurizing the molten solution out of the pipette (FIG. 5A). In case of using liquid glass, no electrical heating is necessary. In-situ high resolution microscope observation during the process will ensure a polymer layer (or liquid glass) with only a couple of micrometers is left inside the pipette. This will eventually form an ion selective membrane. PVC membrane is known to be an ion selective electrode (ISE) for proton ($H^+$) [Al Attas, 2009]. The liquid glass in this project will function also as a proton selective membrane as was proven in a commercialized macroscale glass electrode. The liquid glass droplet out of the tip region was cured at room temperature to form a solid membrane. In the next step, the outer surface of the pipette was coated with silver (Ag) 504. Subsequently, electrolytic deposition of AgCl with chloride the coated Ag electrode (FIG. 5B). Ag/AgCl electrode in this study functions as a pseudo reference electrode. The following half-cell reaction occurs in the pseudo electrode: $AgCl(s)+e^- \leftrightarrow Ag(s)+Cl^-$. A small change in the concentration of $Cl^-$ in the test solution will cause a drift in the pH measurement. In most of biological fluids, the chloride ion concentration remains constant. Thus the potential measurement is expected to have no drift unless there is change in pH.

Figure 5C:
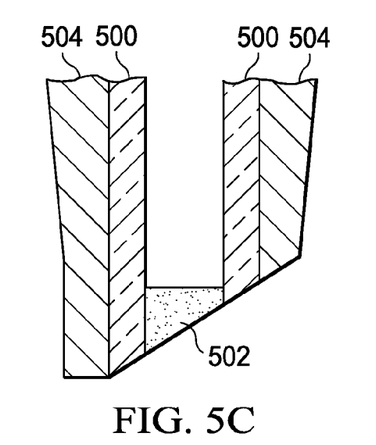
Figure 5D:
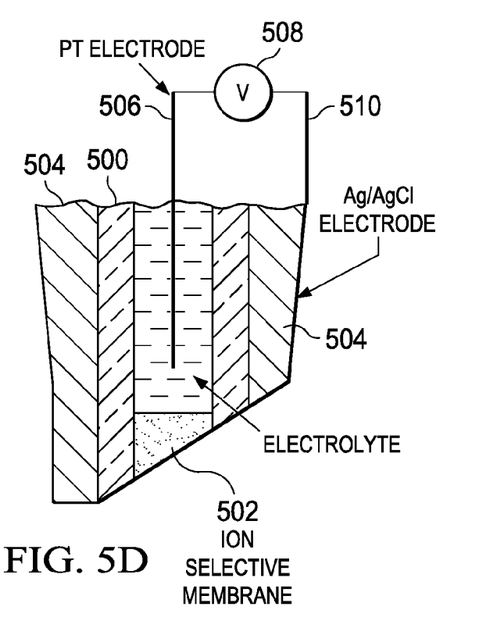
Figure 5E:
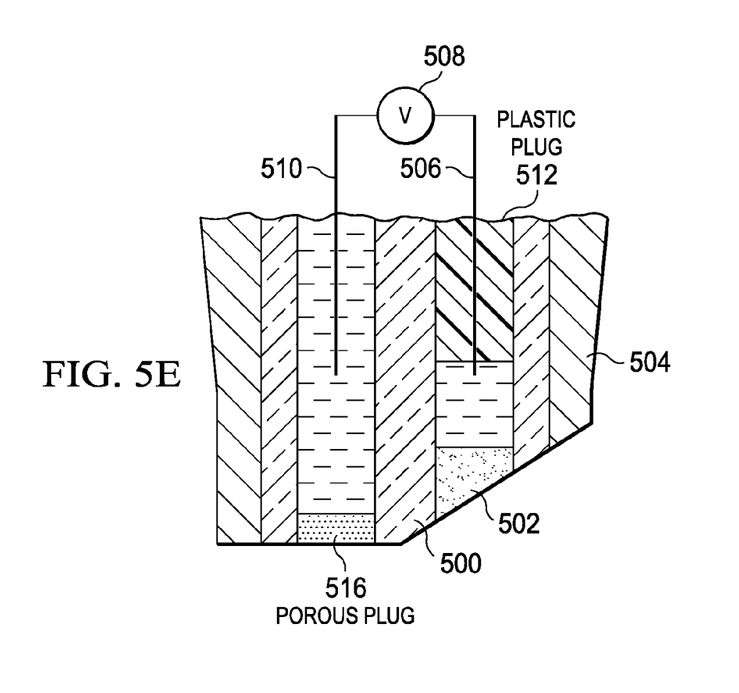

Finally, the pipette was beveled to remove the extruded PVC and the deposited metal (Ag) at the tip of the pipette (FIG. 5C). Another reason of beveling is to control the thickness of the PVC membrane. The fabricated sensor was filled with an electrolyte solution with known pH (i.e. KCl at pH 7). The ionic solution facilitates electron exchange as well as transfer. To increase the sensitivity and stable operation, a Pt electrode 506 was used (see FIGS. 5D and 5E) together with Nat containing Prussian blue [Noll et al., 1998]. As shown in FIG. 5D, a voltage source 508 is connected to the Pt electrode 506 and to Ag/AgCl electrode 504 via line 510. As shown in FIG. 5E, in one embodiment the Pt electrode 506 may be extended through a plastic plug 512 to reach the electrolyte that is located about the ion selective membrane 502. In this embodiment the voltage source 508 is connected to the Pt electrode and to a line 510 that is connected to the electrolyte that is located above a porous plug 516 that is located at the end of the micropipette 500.

PVC ISE can suffer from some shortcomings. Even though ultrasmall volume is detected, the response time may be long due to slow diffusion of proton ion in the polymers. In addition, there may be a need for pre or reconditioning before each measurement. Another possible problem may be interference from other ions, reducing and oxidizing agents [Lin, 2000]. In case that the chloride concentration in the test solution changes, a double barrel micropipette was used (FIG. 5E). This arrangement is a miniaturized version of existing pH sensor. A similar design was introduced by using double-barreled intracellular pH electrode [DeHemptinne et al., 1982]. However, their design involves a few complicated processes. The method of the present invention is highlighted by versatility (by choosing various ISE) and ease in manufacturing of micropipette cell-level sensors. Furthermore, the proposed sensor can be extended to measure other ions including, potassium, calcium, sodium, etc.

Figure 3A:
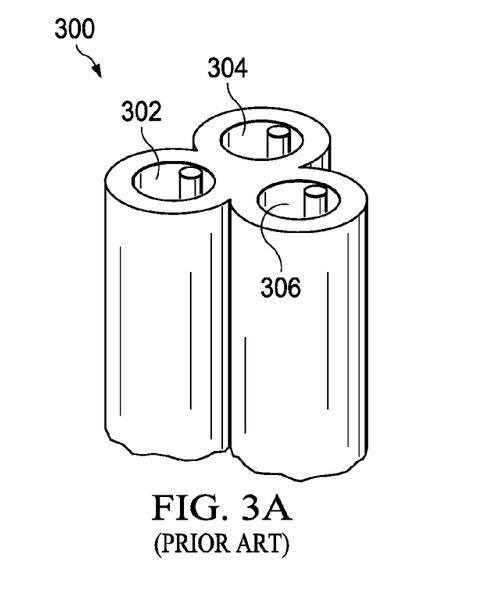
FIG. 3A shows a commercial prior art multibarrel capillary tube.
Figure 3B:
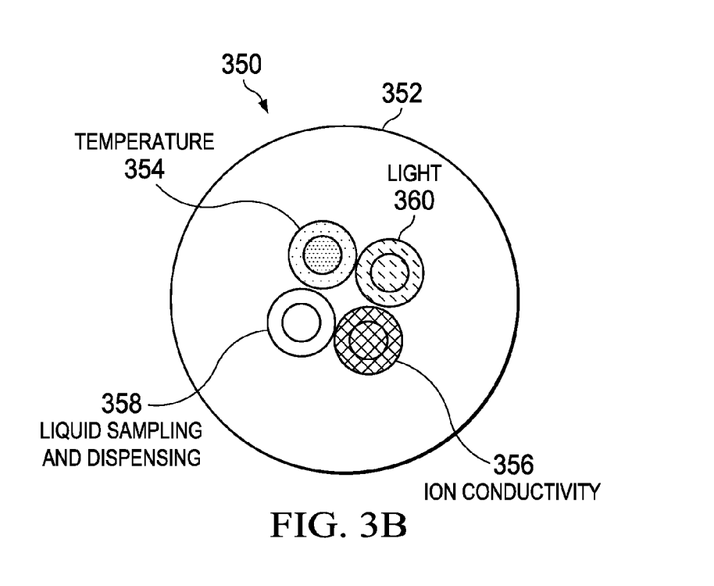
FIG. 3B shows a multifunctional micropipette sensor of the present invention.

The sensors as well as liquid dispenser (with no metals) are realized in one multifunctional micropipette sensor 350 of the present invention as shown in FIG. 3B. The starting material can be, e.g., a commercial prior art multibarrel capillary tube (FIG. 3A) 300 instead of single-barrel tube that is used for individual sensors and dispenser. Tube 300 that is shown in FIG. 3A comprises three separate tubes 302, 304 and 306. The individual components 354, 356, and 360 within tube 352 are integrated into one single multifunctional device where temperature, ion conductivity, pH and light spectroscopy as well as liquid sampling or dispensing (358) are made possible in-situ.

Figure 4:
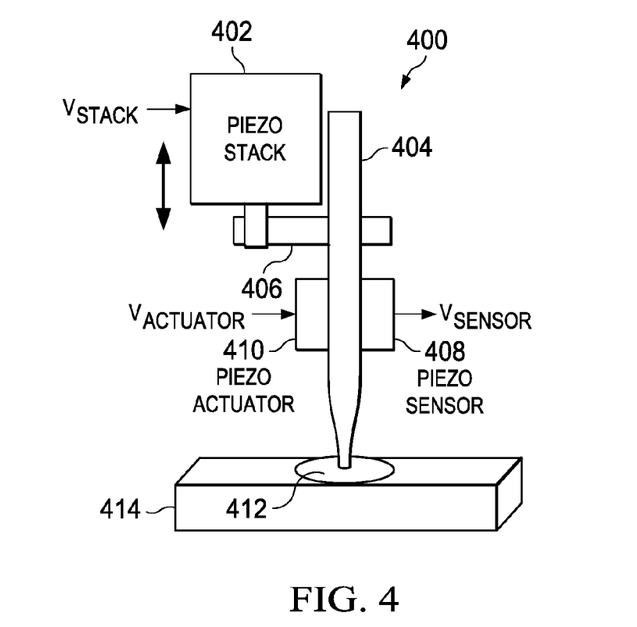
FIG. 4 shows a schematic diagram of a nanoscale tip regulation apparatus that uses the present invention.

FIG. 4 shows a schematic diagram of a nanoscale tip regulation apparatus 400 that uses the present invention. The fundamental measurement principle is scanning probe microscopy. Shear force damping is detected by a piezo sensor 408 and a piezo actuator 410, interpreting the distance between the pipette sensor 404 and a sample 412 that is mounted on a base 414. The pipepette sensor 404 is controlled by piezo stack 402 and actuator 406.

Figure 6:
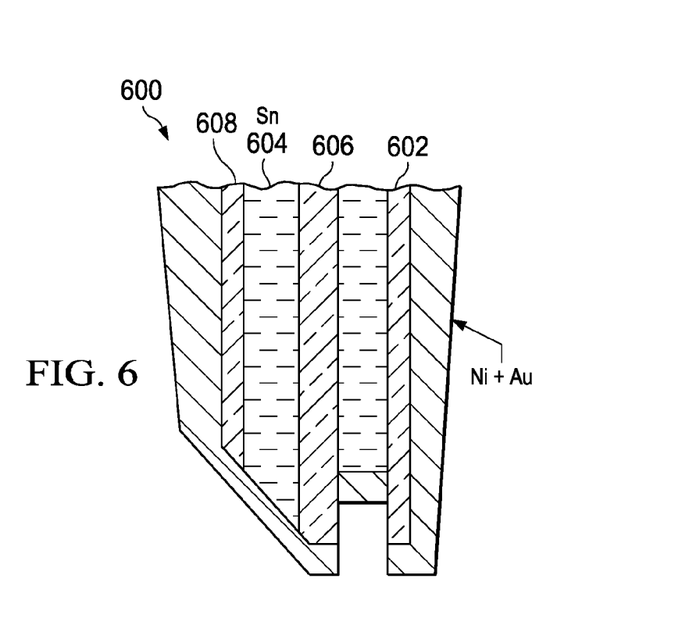
FIG. 6 is a schematic representation of a combined temperature and ion conduction sensor.

Integration of temperature and ion conduction sensors: A schematic outline of an integrated sensor 600 is shown in FIG. 6. Reference numbers 602, 606 and 608 refer to the walls of the micropipette. The metal (e.g. Sn) that is placed in the ion conduction sensor is designated with reference numeral 604. It is important that each sensor in the integrated device should function in the same way as it does in an individual sensor. To ensure this, in the present invention the extruded material (metal) from the interior of the pipette was removed (or grinded in the beveler) to form a sharp interface at the metal-glass tip interface and at the same time, there should be no metal junction for ion conduction sensor. This was realized by precisely controlling the metal extrusion as described previously. The metal 604 filled in the ion conduction sensor should not be extruded from the pipette in this case.

Figure 7A:
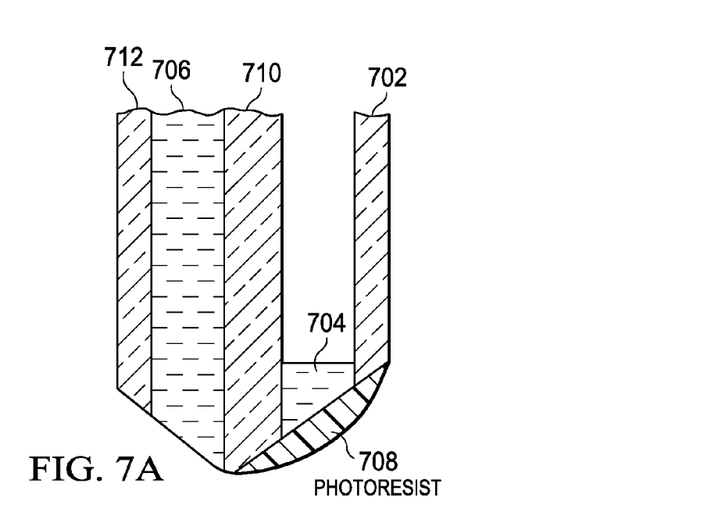
FIGS. 7A and 7B are schematic representations of the fabrication of a combined temperature and pH sensor.
Figure 7B:
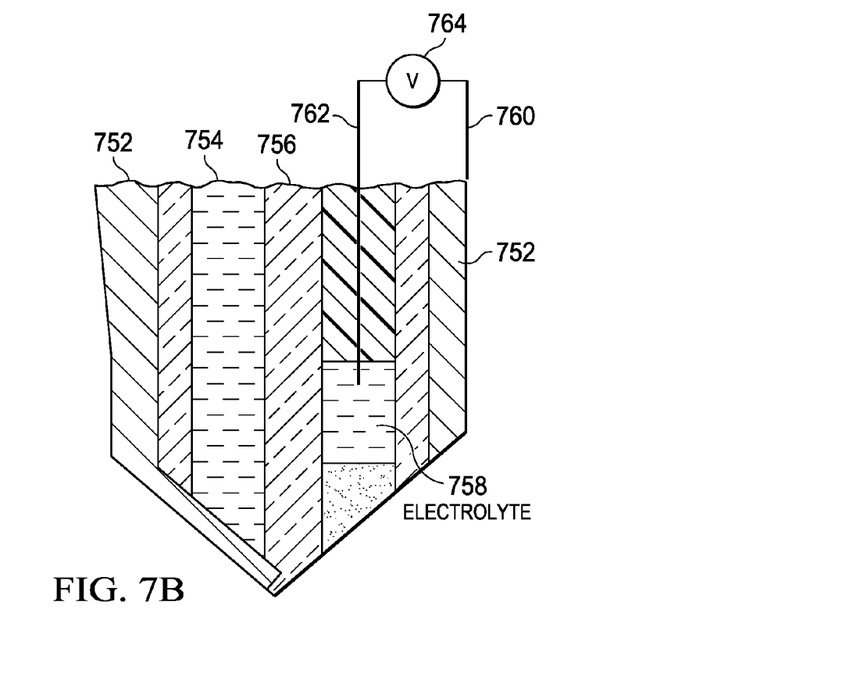

Integration of temperature and pH sensors: On the contrary in the combined temperature and ion conduction sensor, the polymer membrane is kept intact by separating it from the coated metal outside the pipette while the metals must have contact for temperature sensor. To make this possible, the pipette was beveled on both sides of the double barrel pipette as shown in FIGS. 7A and 7B. In FIG. 7A the reference numerals 702, 710 and 712 refer to the walls of the double barrel micropipette. The PVC in the temperature sensor is designated with reference numeral 704. The reference electrode of the pH sensors is designated with reference numeral 706. Then, the beveled area of the PVC side was coated with a photoresist 708 after which metal deposition will be performed. In this way, the beveled area (PVC membrane) was protected from metal deposition. In FIG. 7B reference numeral 756 designates a central wall of the double barrel micropipette. Reference numeral 752 designates the outer metal covering. Reference numeral 754 designates the reference electrode for the pH sensor. Reference numeral 758 designates the electrolyte for the temperature sensor. Reference numeral 764 designates the voltage source. Reference numeral 762 designates a line that connects a first end of the voltage source 764 to the electrolyte 758. Reference numeral 760 designates a line that connects a second end of the voltage source 764 to the outer metal covering 752.

It should be noted that there are two layers of metal deposition: Bi or Ni for thermocouple junction; Ag/AgCl layer for preventing exposure of toxic Ni layer (Bi was not tested in a cell level) and for constructing a reference electrode for pH sensor. The contact between the lead wires and the metal layers are appropriately designed. Non-limiting examples of photoresists include those that are used for thick film applications, e.g., for that generally used to cover a thickness range from 3-20 µm. Other useful characteristics may include low absorption (exposed and unexposed) in the actinic range from 300-450 nm, however, even coatings of 10 µm can be exposed at reasonable exposure doses to form the resist. For example, the photoresist could be of the AZ® 4500-series available from Microchemicals (Germany) or Clariant (Somerville, N.J., USA).

Integration of temperature, ion conduction, and pH sensors: Integration of the aforementioned three sensors into one device is quite challenging. For a successful integration, the beveling was performed on the sides for temperature and pH sensors. It is ensured that the metal inside the pipette for ion conduction sensor is not extruded as explained in the fabrication of the combined temperature and ion conduction sensor. Protecting the PVC membrane was realized using a photoresist. In this way, the three individual sensors were integrated into one single device in the present invention.

Two possible modifications are introduced in the design of the present invention that are different from the previous devices. Fish, et al., used an expensive Pt wire, which is cost-prohibitive and impractical. They inserted Pt microwire into a capillary tube before pulling the micropipette. Watanabe, et al., used plasma enhanced chemical vapor deposition and other thin film technology, which makes the entire fabrication process complicated and practically very expensive. These two sensors are limited to temperature measurement while the proposed sensors can perform multiple functions.

Figure 8:
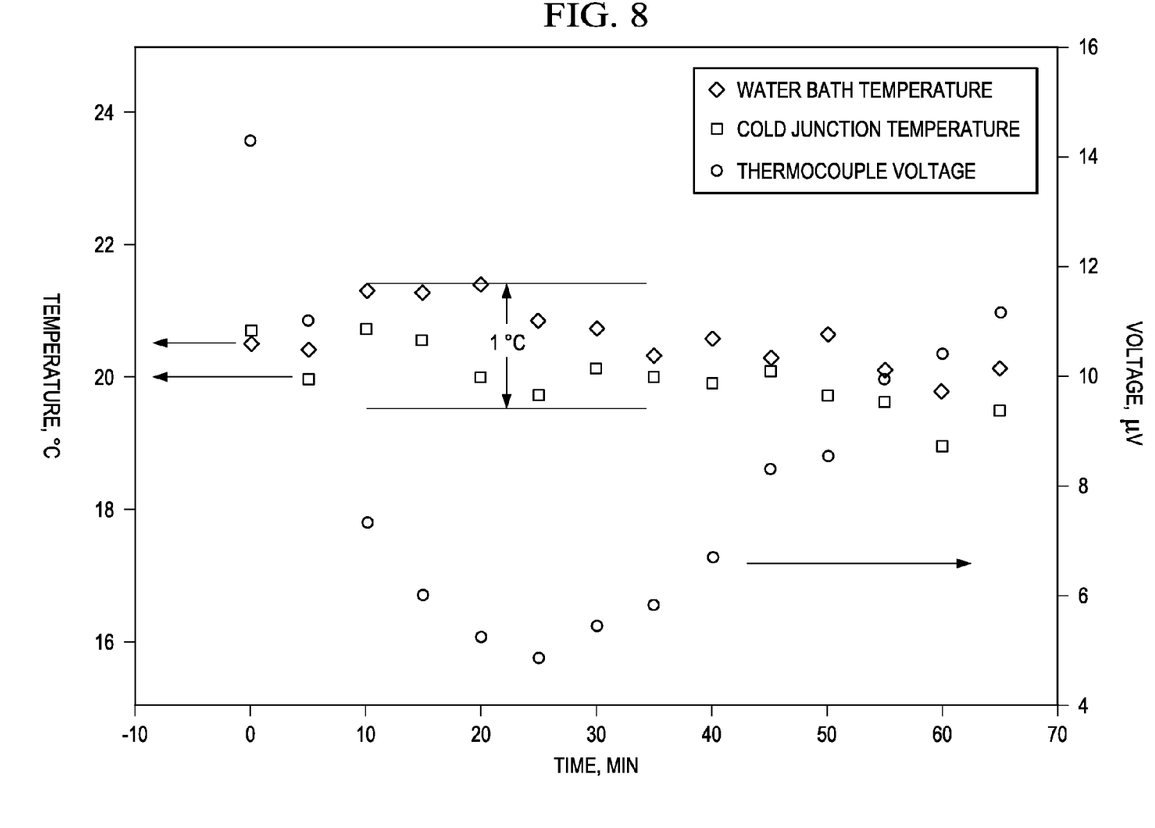
FIG. 8 is a graph of the temperature and voltage over time.

FIG. 8 is a plot of the temperature and voltage over time.

The sensor of the present invention can be used for measuring temperature and ion conduction at the cellular level. The inventors studied ultrafast laser sampling of biological tissue and ion conductivity measurement for studying stress generation mechanisms in plant tissues. The biological sample obtained from laser cutting with a size of 500 µm×500 µm can be directly transferred (in-situ with laser cutting) into a microfabricated chamber for measuring ion conductivity.

Ion conductivity is a signature of cell-death mechanisms caused by various stresses. Being over the critical level of toxic reactive oxygen species in response to a broad range of biotic and abiotic stresses, a cell ruptures and releases ionic species through the cell membrane. These ionic species can be a measure of how a cell responds to various stresses, including heat, light, and toxic chemicals. The inventors tested the device through quantitative analysis by using a microdevice. A microchamber with gold microelectrodes was fabricated by using standard microfabrication technology. A small leaf sample containing ~500 nanoliters of deionized water was inserted into the chamber. The electrodes were used for measuring the ion conductivity of the water. The measurements were carried out a frequency of 130 Hz. Initially high impedance tends to drop within 20 minutes and eventually approaches a constant value signifying the cell's death. The micropipette sensor of the present invention replaces the gold electrodes and can make measurements with a spatial resolution of ~1 µm. The pipette sensor measures temperature with a slight modification of the ion conduction sensors. It measures metabolic thermogenic curves of mitochondria isolated from fish liver tissue. Both sensors are injected into a biological tissue to simultaneously study the metabolism and the effect of the ion. Such studies can be integrated with thermodynamic studies using a thermal activity monitor (TAM 266, Thermogenetics) that is used to determine the enthalpy of hemoglobin under oxidative stress.

The sensor of the present invention can also be combined with the scanning probe microscopy technique in which the tip is made in the nanometer scale. The current technology takes the tip down to, e.g., 0.1, 1, 10, 20, 30, 40, 50, 60, 70, 80, 90 or 100 nanometers, and can be used to measure topography of the sample surface as well as temperature in nanoscale. Another use of the sensor of the present invention is as a microscale, or nanoscale, heating source in a biological sample. When the metal junction has the third metal that has lower conductivity, concentrated heating may be realized in the localized area of the biological sample by supplying electric current or shining infrared laser. Similarly, the sensor can be used as a nanoscale source of plasma. The micro or nanoscale gap between the two metals in case of conductivity sensor can generate plasma inside a small-scale gas environment (such as $O_2$).

The sensor of the present invention can also be used to detect "hot" spots in the semiconductor industry. The sensor can in principle measure temperature of any surface with proper manipulation of the pipette. The sensor can be also used to measure thermophysical properties such as heat capacity or thermal conductivity of unknown liquids.

The sensor of the present invention also provides a novel way of measuring temperature and ion conductivity at the cellular level in-situ. Currently, the dimension of commercially available temperature and ion conduction sensors are far larger than the sensor of the present invention. Cellular activity and stress generation mechanisms in a biological cell have been a great interest to biologists, especially to genetic engineers. Additionally, nanoscale measurement capability combined with scanning probe microscopy technique will be appealing greatly both to industry and academia.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

United States Patent Application No. 20070059215: Micro pipette sensing device.

WIPO Publication No. WO9505000: Probe microscopy.

United States Patent Application No. 20020021222: Sensor measuring field for monitoring micropipette function.

U.S. Pat. No. 5,119,819: Method and apparatus for non-invasive monitoring of blood glucose.

Fish, G., Bouevitch, O., Kokotov, S., Lieberman, K., Palanker, D., Turovets, I., Lewis, A., "Ultrafast response micropipette-based submicrometer thermocouple," Rev. Sci. Instrum. 66 (5), 3300 (1995).

Watanabe, M. S., Kakuta, N., Mabuchi, K., Yamada, Y., "Micro-thermocouple probe for measurement of cellular thermal responses," Proc. IEEE, Engineering in Medicine and Biology 27$^{th}$ Annual Conference (2005).

What is claimed is:

1. A micropipette thermal sensor comprising:
   a multibarrel capillary tube;
   one or more glass micropipettes, wherein each of the one or more micropipettes is enclosed within the multibarrel capillary tube;
   a first metal that fills a hollow central portion of each of the one or more micropipettes wherein the first metal is a low melting-temperature alloy that has a melting point that is lower than a melting point of glass in the one or more glass micropipettes;
   a second metal that is coated on an outer surface of each of the one or more micropipettes; and
   a metal junction between the first metal and the second metal at the tip of each of the one or more micropipettes.

2. The micropipette thermal sensor of claim 1, wherein the second metal that is coated on the outer surface comprises one or more noble metals like silver, gold, bismuth, titanium, or platinum.

3. The micropipette thermal sensor of claim 1, wherein the metal junction at the tip comprises a Sn:Pb alloy.

4. The micropipette thermal sensor of claim 1, wherein the micropipette thermal sensor is used to measure a temperature or a temperature change in a semiconductor, a biological system, a biological fluid, a biological cell, and a biological tissue.

5. The micropipette thermal sensor of claim 1, wherein the metal junction between the first metal and the second metal at the tip of each of the one or more micropipettes is beveled.

6. A multifunctional micropipette sensor comprising:
   a multibarrel capillary tube;
   three or more glass micropipettes, wherein each of the three or more micropipettes is enclosed within the multibarrel capillary tube;
   a first metal that fills a hollow central portion of each of the three or more micropipettes wherein the first metal is a low melting-temperature alloy that has a melting point that is lower than a melting point of glass in the one or more glass micropipettes;
   a second metal that is coated on the outer surface of each of the three or more micropipettes;
   a metal junction between the first metal and the second metal at the tip of each of the three or more micropipettes; and
   a polymer coating at the tip of at least one of the three or more micropipettes.

7. The multifunctional micropipette sensor of claim 6, wherein the sensor is used for measurement of a temperature, an ion conductivity, an optical property, and for dispensing a liquid, wherein the measurement is made concurrently or individually.

8. The multifunctional micropipette sensor of claim 6, wherein the multifunctional micropipette sensor is used for localized heating of a biological system or a biological sample.

9. The multifunctional micropipette sensor of claim 6, wherein the multifunctional micropipette is used as a plasma source.

10. The micropipette thermal sensor of claim 6, wherein the metal junction between the first metal and the second metal at the tip of each of the one or more micropipettes is beveled.

* * * * *